(12) United States Patent
Anderson et al.

(10) Patent No.: US 7,708,766 B2
(45) Date of Patent: May 4, 2010

(54) DISTRACTION SCREW

(75) Inventors: David Greg Anderson, Charlottesville, VA (US); Conor McCrea, Dedham, MA (US); Christopher Ramsay, New Bedford, MA (US)

(73) Assignee: DePuy Spine, Inc., Raynham, MA (US)

( * ) Notice: Subject to any disclaimer, the term of this patent is extended or adjusted under 35 U.S.C. 154(b) by 0 days.

(21) Appl. No.: 10/638,821

(22) Filed: Aug. 11, 2003

(65) Prior Publication Data

US 2005/0038438 A1  Feb. 17, 2005

(51) Int. Cl.
*A61B 17/86* (2006.01)
(52) U.S. Cl. .................. 606/301; 606/105
(58) Field of Classification Search ............ 606/72, 606/73, 76, 61, 90; 411/263, 308, 395, 411, 411/412, 413, 415, 426
See application file for complete search history.

(56) References Cited

U.S. PATENT DOCUMENTS

| | | | |
|---|---|---|---|
| 408,531 A * | 8/1889 | Rogers ................ 411/413 |
| 2,382,019 A | 8/1945 | Miller |
| 2,801,631 A * | 8/1957 | Charnley ................ 606/65 |
| 3,174,387 A | 3/1965 | Fischer |
| 3,233,500 A * | 2/1966 | Vellier ................ 411/413 |
| 3,717,067 A * | 2/1973 | Vick et al. ............. 411/455 |
| 3,896,504 A | 7/1975 | Fischer |
| 4,013,071 A * | 3/1977 | Rosenberg ............... 606/73 |
| 4,027,573 A * | 6/1977 | Laverty ................ 411/413 |
| 4,059,102 A * | 11/1977 | Devas .................... 606/73 |
| 4,175,555 A | 11/1979 | Herbert |
| 4,621,963 A * | 11/1986 | Reinwall ............... 411/369 |
| 4,716,893 A | 1/1988 | Fischer et al. |
| 4,917,704 A | 4/1990 | Frey et al. |
| 4,938,773 A * | 7/1990 | Strand ................ 623/23.15 |
| 4,950,270 A * | 8/1990 | Bowman et al. ........... 606/72 |
| 4,955,908 A | 9/1990 | Frey et al. |
| 5,019,079 A | 5/1991 | Ross |
| 5,034,011 A | 7/1991 | Howland |
| 5,059,193 A | 10/1991 | Kuslich |
| 5,108,404 A | 4/1992 | Scholten et al. |
| 5,122,133 A | 6/1992 | Evans |
| 5,176,678 A | 1/1993 | Tsou |

(Continued)

FOREIGN PATENT DOCUMENTS

AU  516 581 B2  6/1981

(Continued)

*Primary Examiner*—Eduardo C Robert
*Assistant Examiner*—David Comstock
(74) *Attorney, Agent, or Firm*—Nutter McClennen & Fish LLP

(57) ABSTRACT

A simple, safe implantable bone screw, and a method for distracting two bone segments, is provided. In general, the bone screw includes a shank having a threaded proximal portion and a distal portion with a major diameter that is less than a minor diameter of the threaded proximal portion. A transitional region of decreasing diameter can be disposed between the threaded proximal portion and the distal portion, and a driver receiving element is preferably disposed on a proximal end of the bone screw. In use, the proximal and distal portions of the bone screw are adapted to engage two segments of bone, and to create a distraction force between the two segments of bone.

11 Claims, 7 Drawing Sheets

U.S. PATENT DOCUMENTS

| | | | |
|---|---|---|---|
| 5,222,954 A * | 6/1993 | Baker et al. ................... 606/61 |
| 5,258,031 A | 11/1993 | Salib et al. |
| 5,263,803 A | 11/1993 | Anquetin |
| 5,403,136 A * | 4/1995 | Mathys ........................ 411/310 |
| 5,425,772 A | 6/1995 | Brantigan |
| 5,480,440 A | 1/1996 | Kambin |
| 5,489,210 A * | 2/1996 | Hanosh ...................... 433/173 |
| 5,496,322 A | 3/1996 | Matthews |
| 5,536,127 A * | 7/1996 | Pennig ........................ 411/413 |
| 5,580,352 A * | 12/1996 | Sekel ........................ 623/22.46 |
| 5,593,410 A * | 1/1997 | Vrespa ......................... 606/73 |
| 5,653,762 A | 8/1997 | Pisharodi |
| 5,653,763 A | 8/1997 | Errico et al. |
| 5,702,479 A * | 12/1997 | Schawalder .............. 623/23.15 |
| 5,722,977 A | 3/1998 | Wilhelmy |
| 5,725,527 A | 3/1998 | Biederman et al. |
| 5,725,595 A * | 3/1998 | Gustilo .................... 623/23.15 |
| 5,766,251 A | 6/1998 | Koshino |
| 5,772,663 A | 6/1998 | Whiteside et al. |
| 5,827,285 A | 10/1998 | Bramlet |
| 5,836,948 A | 11/1998 | Zucherman et al. |
| 5,899,940 A | 5/1999 | Carchidi et al. |
| 5,964,761 A | 10/1999 | Kambin |
| 5,971,985 A * | 10/1999 | Carchidi et al. .............. 606/61 |
| 5,997,541 A * | 12/1999 | Schenk ........................ 606/73 |
| 6,001,101 A * | 12/1999 | Augagneur et al. ......... 606/316 |
| 6,008,433 A | 12/1999 | Stone |
| 6,018,094 A | 1/2000 | Fox |
| 6,030,162 A * | 2/2000 | Huebner ..................... 411/413 |
| 6,053,653 A | 4/2000 | Tanaka et al. |
| 6,077,268 A | 6/2000 | Farris et al. |
| 6,099,531 A | 8/2000 | Bonutti |
| 6,125,526 A * | 10/2000 | Wierzchon ................ 29/525.02 |
| 6,129,763 A | 10/2000 | Chauvin et al. |
| 6,224,599 B1 | 5/2001 | Baynham et al. |
| 6,248,106 B1 | 6/2001 | Ferree |
| 6,270,501 B1 | 8/2001 | Freiberg et al. |
| 6,280,191 B1 | 8/2001 | Gordon |
| 6,306,140 B1 * | 10/2001 | Siddiqui ....................... 606/73 |
| 6,306,143 B1 | 10/2001 | Kvarnstrom et al. |
| 6,358,254 B1 | 3/2002 | Anderson |
| 6,402,750 B1 | 6/2002 | Atkinson et al. |
| 6,428,256 B2 | 8/2002 | Wiesner |
| 6,696,073 B2 * | 2/2004 | Boyce et al. ................. 424/422 |
| 6,743,231 B1 | 6/2004 | Gray |
| 6,746,449 B2 | 6/2004 | Jones |
| 2002/0049447 A1 | 4/2002 | Li |
| 2003/0004517 A1 | 1/2003 | Andreson |
| 2003/0028251 A1 | 2/2003 | Matthews |
| 2003/0055433 A1 | 3/2003 | Krenkel et al. |
| 2003/0212400 A1 * | 11/2003 | Bloemer et al. ............... 606/61 |

FOREIGN PATENT DOCUMENTS

| | | | |
|---|---|---|---|
| DE | 20216048 | | 1/2003 |
| WO | WO 00/38586 | * | 7/2000 |
| WO | 0221994 | | 3/2002 |
| WO | 03002038 | | 1/2003 |
| WO | 03032863 | | 4/2003 |

* cited by examiner

DISTRACTION SCREW

FIELD OF THE INVENTION

The present invention relates to a bone screw for distracting two segments of bone, and in particular to an implantable bone screw for use in spinal surgery to expand the spinal canal.

BACKGROUND OF THE INVENTION

U.S. Pat. No. 6,358,254 to Anderson, the disclosure of which is incorporated by reference, describes spinal stenosis as a condition that inflicts millions of people with back and leg pain due to compression of spinal nerves. Severe cases often require surgery to relieve nerve compression and lessen the back and leg pain. A spinal laminectomy is the traditional operation performed to treat spinal stenosis. In this operation, the posterior aspects of the spinal column are removed to "unroof" the spinal canal and relieve the pressure on the nerves. Specifically, the spinous processes, lamina and portions of the facet joints are excised to relieve the nerve root compression.

Although a spinal laminectomy is often successful in relieving pressure on the nerves of the spinal canal, several disadvantages can be associated with the laminectomy. First, the laminectomy removes important sites of back muscle attachment which may lead to back muscle dysfunction and pain. Second, the laminectomy exposes the nerve sac which may cause scar tissue to form around the nerves, leading to recurrent pain. Third, the laminectomy can destabilize the spine resulting in a forward slippage of one vertebra on another, which can cause recurrent pain and deformity. Fourth, the laminectomy requires a large surgical exposure and significant blood loss, making the laminectomy less favorable for older patients. Finally, spinal stenosis can recur following the laminectomy, requiring revision surgery.

Laminectomy risks have led surgeons to seek an alternative for patients with severe spinal stenosis. Some surgeons have used multiple laminotomies to treat spinal stenosis. Laminotomies involve removing bone and soft tissue from the posterior aspect of the spine making "windows" into the spinal canal over areas of nerve compression. Multiple laminotomies remove less tissue than the laminectomy, resulting in less scarring, vertebral instability, and blood loss. However, laminotomies also have associated disadvantages. Laminotomies may not adequately relieve nerve compression and therefore the pain may not be fully abated. Moreover, laminotomies are more difficult to correctly perform than the laminectomy, and they still expose the nerves causing nerve scarring. Patients receiving multiple laminotomies also often have recurrent spinal stenosis requiring revision surgery.

For the foregoing reasons, there is a need for improved methods and devices for relieving the symptoms of spinal stenosis without the drawbacks of currently available techniques. More particularly, simple, safe, effective, and permanent methods and devices are needed to expand the spinal canal to relieve the pressure on the spinal nerves.

SUMMARY OF THE INVENTION

The present invention provides a simple, safe implantable bone screw and method for distracting two segments of bone, and preferably for expanding the spinal canal area to provide additional space for the spinal nerves, relieving pressure on the spinal nerves. In one embodiment, the bone screw includes a shank having a threaded proximal portion and a distal portion with a major diameter that is less than a minor diameter of the threaded proximal portion. The proximal and distal portions of the shank are configured to create a distraction force therebetween when inserted into two segments of bone.

In another embodiment, the distal portion of the bone screw can include a thread formed thereon which preferably has a pitch that is less than a pitch of the thread on the threaded proximal portion. The thread on the threaded proximal portion can, however, have a pitch that varies along a length of the proximal portion. By way of a non-limiting example, the pitch of the thread can gradually and progressively decrease from the proximal portion of the screw to the distal portion of the screw. While the distal portion of the bone screw is preferably threaded, it can have a variety of other configurations. By way of non-limiting example, the distal portion of the shank can be removably mated to the proximal portion, and the proximal portion can be adapted to mate to the distal portion such that at least a portion of the distal portion expands upon engagement by the proximal portion. In another embodiment, a major diameter of the distal portion can decrease in a proximal-to-distal direction. By way of non-limiting example, the distal portion can have a stepped diameter such that the diameter incrementally decreases in a proximal-to-distal direction. Alternatively, or in addition, the distal portion can include at least one surface feature formed thereon and adapted to engage bone.

In yet another embodiment, a bone screw is provided having a shank with a proximal portion having at least one thread formed thereon. The thread(s) has a first pitch in a proximal region of the proximal portion and a second pitch in a distal region of the proximal portion. The shank also includes a distal portion having at least one thread formed thereon with a third pitch. The second pitch is proximate in size to the third pitch and is distinct in size from the first pitch.

The present invention also provides a method of expanding the spinal canal using a bone screw having a shank including proximal and distal portions that are configured to create a distraction force therebetween when inserted into two portions of bone. The method includes the steps of forming a hole in the pedicle of a vertebrae, cutting the pedicle to form two bone portions, and advancing the bone screw into the hole, wherein the proximal and distal portions of the bone screw expand the distance between the two bone portions.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a bone screw for distracting two pieces of bone, and more preferably for expanding a spinal canal. In general, the bone screw includes a shank having a proximal and distal portions that are adapted to engage two segments of bone, and to create a distraction force between the two segments of bone. The bone screw is particularly advantageous in that it is easy to use, it maintains normal anatomic structures and muscle attachments, and it can be efficiently implanted, thereby reducing the time and expense necessary to perform spinal surgery.

Figure 1A:
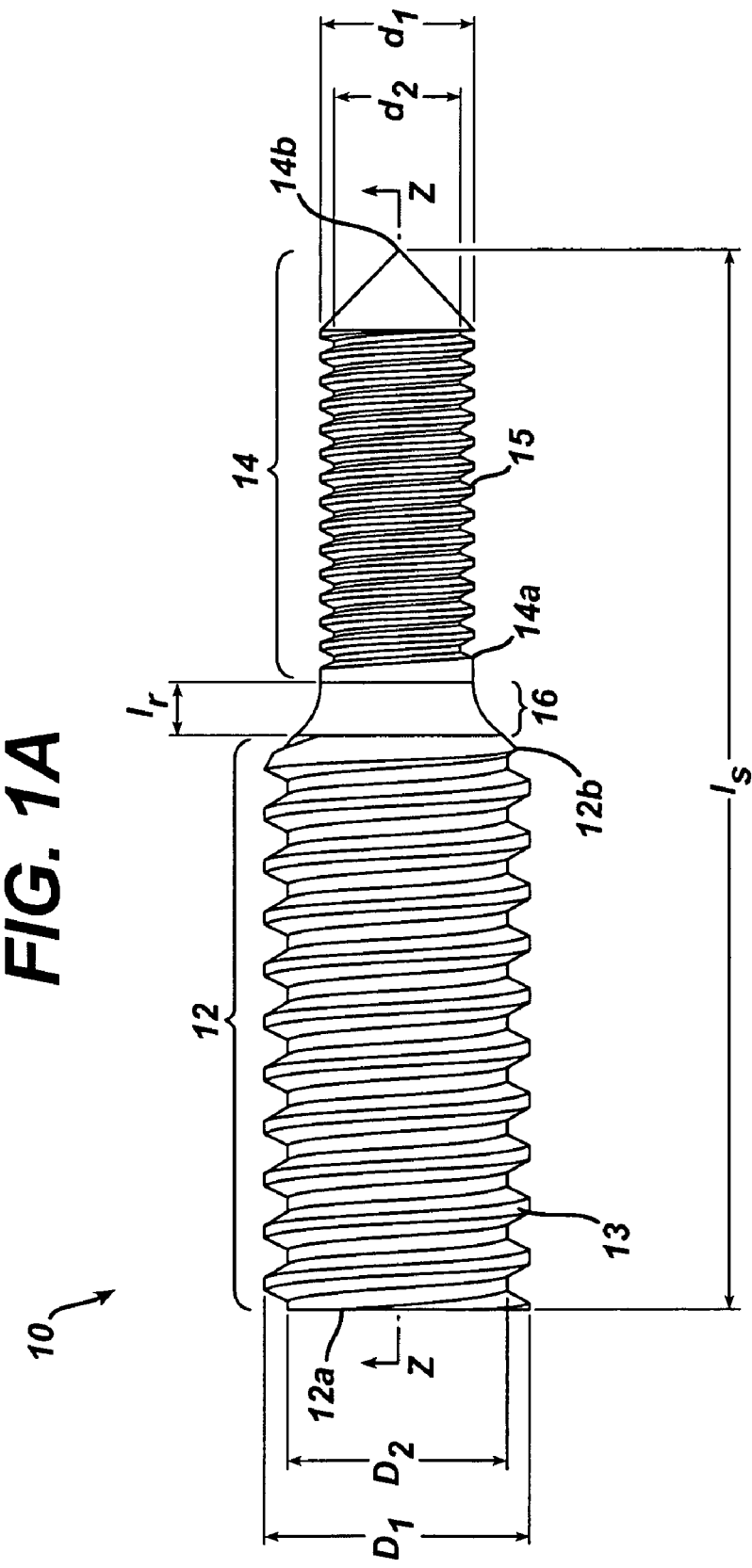
FIG. 1A is a perspective view of a bone screw according to one embodiment of the present invention.
Figure 1B:
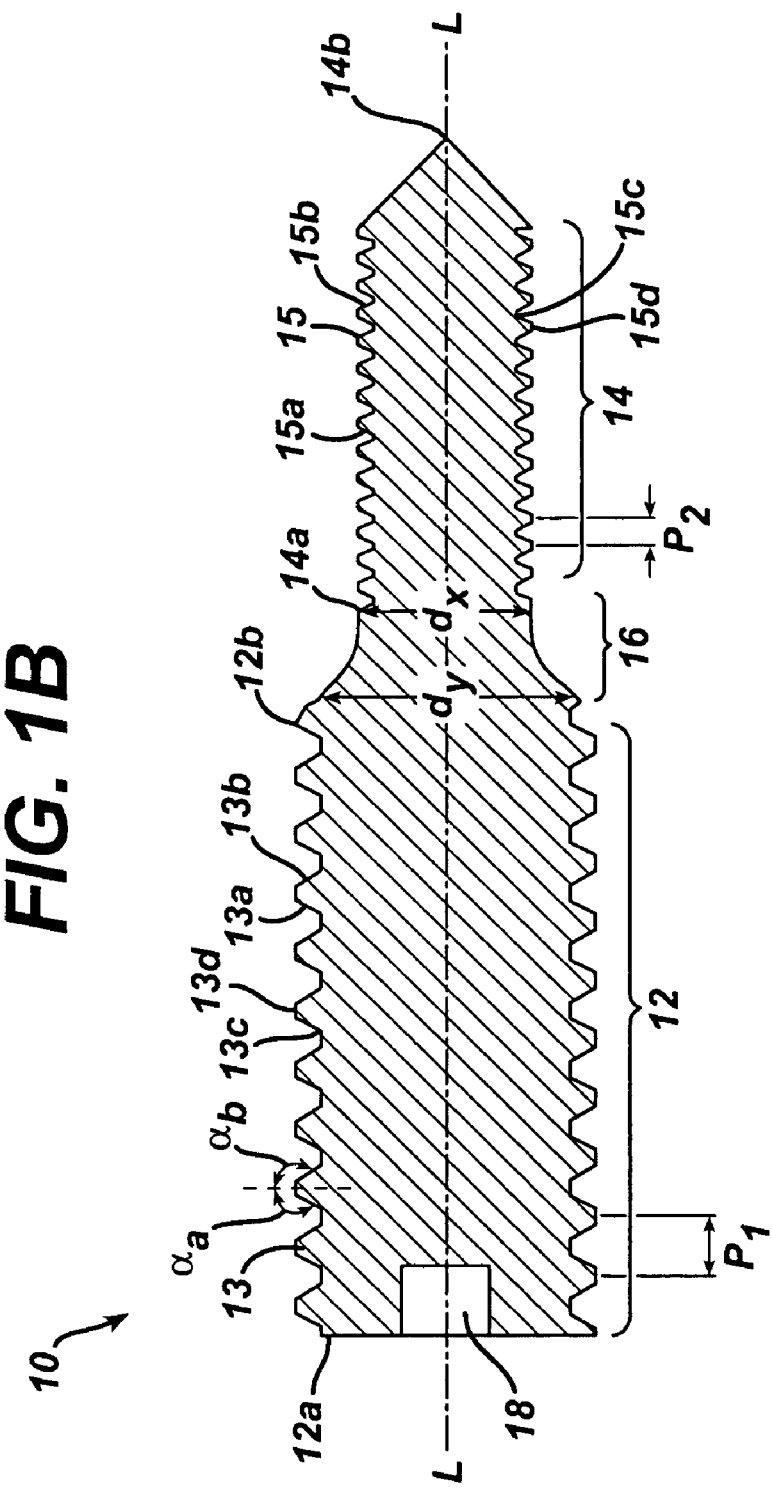
FIG. 1B is a cross-sectional view of the bone screw shown in FIG. 1A taken across line 2—2.
Figure 1C:
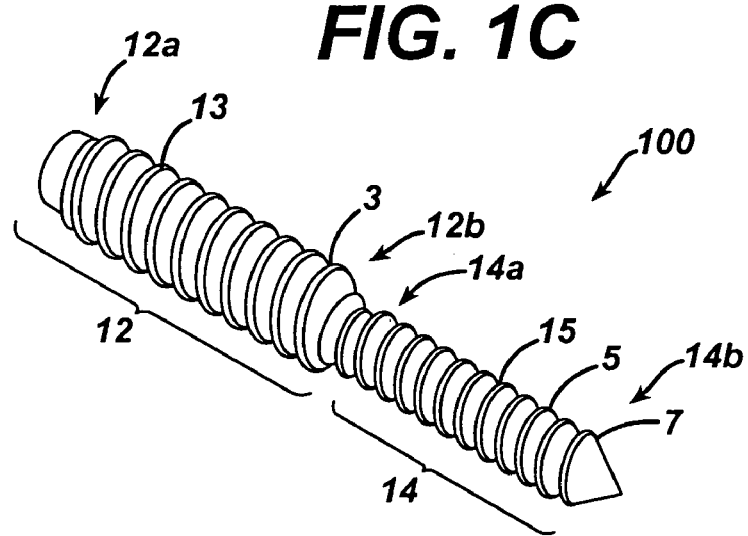
FIG. 1C is a perspective view of the bone screw shown in FIG. 1A having self-tapping threads formed thereon in accordance with another embodiment of the present invention.

FIGS. 1A–1C illustrate one embodiment of a bone screw 10 in accordance with the present invention. As shown, the bone screw 10 includes a shank having a proximal portion 12 with at least one thread 13 formed thereon, a distal portion 14, and a transitional region 16, optionally of decreasing diameter, disposed between the threaded proximal portion 12 and the distal portion 14. The overall size of the bone screw 10 can vary depending on the intended use, but it preferably has a size that allows the bone screw 10 to be implanted through a pedicle of a vertebra. In an exemplary embodiment, where the bone screw 10 is used in spinal applications, the bone screw 10 has a length $l_s$ that is in the range of about 8 mm to 100 mm.

The proximal portion 12 of the bone screw 10 can have a variety of configurations, shapes, and size. As previously stated, the proximal portion 12 preferably includes at least one thread 13 formed thereon. In an exemplary embodiment, the thread 13 extends from the proximal end 12a, or from a point adjacent to the proximal end 12a, and it terminates at or adjacent to the transition region 16. The start of the thread 13 at the distal end 12b of the proximal portion 12 can optionally be self-tapping to facilitate engagement between the proximal portion 12 and bone. By way of non-limiting example, FIG. 1C illustrates bone screw 100 having a self-tapping feature 3 formed in thread 13 at the distal end 12b of the proximal portion 12.

Referring back to FIG. 1B, the thread 13 on the proximal portion 12 includes proximal- and distal-facing flanks 13a, 13b which extend between a root 13c and a crest 13d. Each flank 13a, 13b can vary in shape and size, and each flank 13a, 13b can extend at a variety of angles $\alpha_a$, $\alpha_b$, with respect to the longitudinal axis L. By way of non-limiting example, the flanks 13a, 13b can converge toward one another, as shown, or in other embodiments (not shown) they can be parallel to one another, or can diverge from one another at different angles. The crest 13d of the thread 13 can also have a variety of shapes and can be, for example, pointed to form a sharp edge, or it can be beveled, as shown. Exemplary thread forms include square threads, buttress threads, cancellous bone threads, cortical bone threads, or some combination of these.

In the exemplary embodiment illustrated in FIGS. 1A–1C, the size, shape, and pitch of the thread remains constant along at least a substantial length of the proximal portion 12. In other embodiments, however, the size, shape, and pitch of the thread may be varied along at least a portion of the length of the proximal portion 12. As shown in FIG. 1A, the proximal portion 12 has a minor diameter $D_2$ measured from the root 13c of the thread 13 and a major diameter $D_1$ measured from the crest 13d of the thread 13. The thread 13 can also have a pitch $P_1$ that remains substantially constant along a substantial length of the proximal portion 12, such that the thread 13 has uniform spacing along the axis L between each thread form. In an exemplary embodiment, where the bone screw 10 is used in spinal applications, the minor diameter $D_2$ of proximal portion 12 is in the range of about 2 mm to 9 mm, the major diameter $D_1$ is in the range of about 3 mm to 12 mm, and the pitch $P_1$ of the thread 13 is in the range of about 1 to 12.

Still referring to FIGS. 1A–1C, the distal portion 14 of the bone screw 10 can also have a variety of configurations. In an exemplary embodiment, the distal portion 14 includes a thread 15 formed thereon having proximal- and distal-facing flanks 15a, 15b that extend between a root 15c and a crest 15d. The shape, size, and pitch of the thread 15 along the distal portion 14 can vary, as previously described with respect to thread 13 formed on the proximal portion 12. In one embodiment, the distal portion 14 has a minor diameter $d_2$, measured from the root 15c of the thread 15 and a major diameter $d_1$, measured from the crest 15d of the thread 15. The major diameter $d_1$ of the distal portion 14 is preferably less than the major diameter $D_1$ of the proximal portion 12. This is particularly advantageous in that it prevents the distal portion 14 from creating a bone tunnel larger than the proximal portion 12, thereby allowing the proximal portion 12 to engage bone which the distal portion 14 has already passed through. The thread 15 on the distal portion 14 also may have a pitch $P_2$ that is smaller than the pitch $P_1$ of the proximal thread 13. This allows the proximal portion 12 of the bone screw to advance more quickly into bone than the distal portion 14, thereby creating a distraction force between the proximal and distal portions 12, 14. By way of non-limiting example, the thread 13 on the proximal portion 12 can have a pitch $P_1$ that is twice the pitch $P_2$ of the thread 15 on the distal portion 14. As a result, the proximal portion 12 will advance into bone twice as fast as the distal portion 14 advances. In an exemplary embodiment, where the bone screw 10 is used in spinal applications, the minor diameter $d_2$ of distal portion 14 is in the range of about 1 mm to 8 mm, the major diameter $d_1$ is in the range of about 3 mm to 10 mm, and the pitch $P_2$ of the thread 15 is in the range of about 0 to 10.

Although the proximal portion 12 and the distal portion 14 of the exemplary embodiment illustrated in FIGS. 1A–1C each include a single thread, a person skilled in the art will appreciate that the proximal portion 12 and the distal portion 14 may include any number of threads of varying or uniform size, shape, and pitch.

The distal portion 14 of the bone screw 10 further includes an apex 14b formed at the distal-most end of the screw 10. The apex 14b can have a variety of configurations, and by way of non-limiting example, the apex 14b can be in the form of a cone-type or gimlet-type tip. As shown in FIG. 1A, the apex 14b of the screw 10 is in the form of a cone-type type, wherein the thread 15 terminates at a position proximal to the distal tip 14b and the core of the screw 10 is formed into a solid, cone-like structure. With a gimlet tip, the thread(s) extend to and merge at the distal tip of the screw. A person skilled in the art will appreciate that either tip can be used, or alternatively the apex 14b can have a variety of other configurations. The apex 14b, as well as the remainder of the screw 10, can also optionally be configured into a self-tapping and/or self-drilling bone screw to avoid the need to tap the bone screw and/or pre-drilled a hole in the bone. By way of non-limiting example, FIG. 1C illustrates a self-tapping feature 5 formed in thread 15 near the distal end 14b of the distal portion 14, and another self-tapping feature 7 formed in the apex 14b. A person skilled in the art will appreciate that a variety of self-tapping and/or self-drilling features can be used.

As previously stated, the bone screw 10 can also include a transition region 16 extending between the proximal and distal portions 12, 14. The transition region 16 is preferably an unthreaded area of the shank having a diameter that decreases from the proximal portion 12 of the screw 10 to the distal portion 14 of the screw 10. As shown in FIG. 1B, the transition region 16 has a proximal diameter $d_y$ that is greater than a distal diameter $d_x$, and the surface of the transition region 16 extending therebetween along the length $l_t$ of the transition region 16 is preferably sloped. The sloped transition region 16 provides improved performance and allows for ease of manufacture of a screw having differing diameters and pitches. While a sloped transition region 16 is shown, the transition region 16 can have virtually any configuration, shape, and size, such as, for example, a stepped or non-tapered configuration. In an exemplary embodiment (not shown), the length $l_t$ of the transition region 16 is as small as possible to ensure that the proximal thread 13 will engage, rather than strip, bone.

In order to facilitate implantation of the bone screw 10, a driver receiving element 18 (FIG. 1B) can be formed on or attached to the proximal end 12a of the screw 10 for mating with a driver tool (not shown) for driving the bone screw 10 into bone. The driver receiving element 18 can have a variety of configurations, but in an exemplary embodiment the driver receiving element 18 is in the form of a socket formed in the proximal-most end 12a of the proximal portion 12. The socket 18 can have virtually any shape and size, and can be, for example, a hexagonal-shaped socket for receiving a hexagonally-shaped driver member. Alternatively, the proximal portion 12 can include a hexagonal-shaped head formed thereon for fitting with a hexagonal shaped socket in a driver tool. A person skilled in the art will appreciate that a variety of driver receiving elements can be used, and/or the proximal end 12a of the bone screw 10 can have virtually any other configuration. In other embodiments, the bone screw 10 can optionally be cannulated, e.g., include a lumen extending therethrough, for receiving a guide wire.

FIGS. 2–5 illustrate additional embodiments of bone screws according to the present invention. For reference purposes, like reference numbers are used to refer to like parts. A person skilled in the art will appreciate that a bone screw in accordance with the present invention can include any combination of features described and/or shown herein, as well as other features known in the art. The bone screw of the present invention is not intended to be limited to the particular embodiments illustrated.

Figure 2:
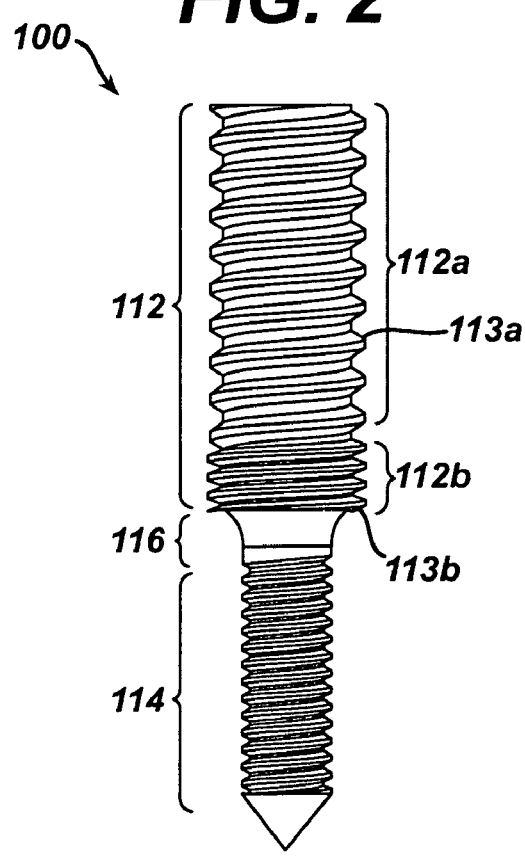
FIG. 2 is a perspective view of another embodiment of a bone screw in accordance with the present invention.

FIG. 2 illustrates one embodiment of a bone screw 100 in which the proximal portion 112 includes one or more threads formed thereon and having varying thread forms to help achieve fixation of the screw with the bone before and/or during distraction. In particular, as shown, the bone screw 100 includes a proximal portion 112 having proximal and distal regions 112a, 112b that have thread(s) 113a, 113b with different pitches. The thread(s) 113a, 113b in each region 112a, 112b can be formed from a single thread that extends along the entire length of the proximal portion 112, or alternatively the proximal portion 112 can include any number of threads, such as first and second threads formed in the proximal and distal regions 112a, 112b, respectively. As shown in FIG. 2, the thread 113b in the distal region 112b of the proximal portion 112, has a reduced pitch, such that the pitch of the thread 113a in the proximal region 112a of the proximal portion 112 is greater than the pitch of the thread 113b in the distal region 112b of the proximal portion 112. In an exemplary embodiment, the pitch of the thread 113b in the distal region 112b is equal to the pitch of a thread 15 formed on the distal portion 14 of the screw, as will be discussed in more detail below. The thread form in the distal region 112b of the proximal portion 112 can also vary, and in an exemplary embodiment the thread 113b is intermittently disposed on the proximal portion 112, and it is at least partially barbed, such that the proximal-facing flank is substantially planar and the distal-facing flank is curved. The configuration of the embodiment shown in FIG. 2 is particularly advantageous in that it allows the thread 113b in the distal region 112b of the proximal portion 112 to engage the bone before a distraction force is created between the proximal and distal portions 112, 114, which will also be discussed in more detail below. Moreover, the barbed shape of the thread 113b will help inhibit back-out of the bone screw 100 upon insertion into bone.

Figure 3:
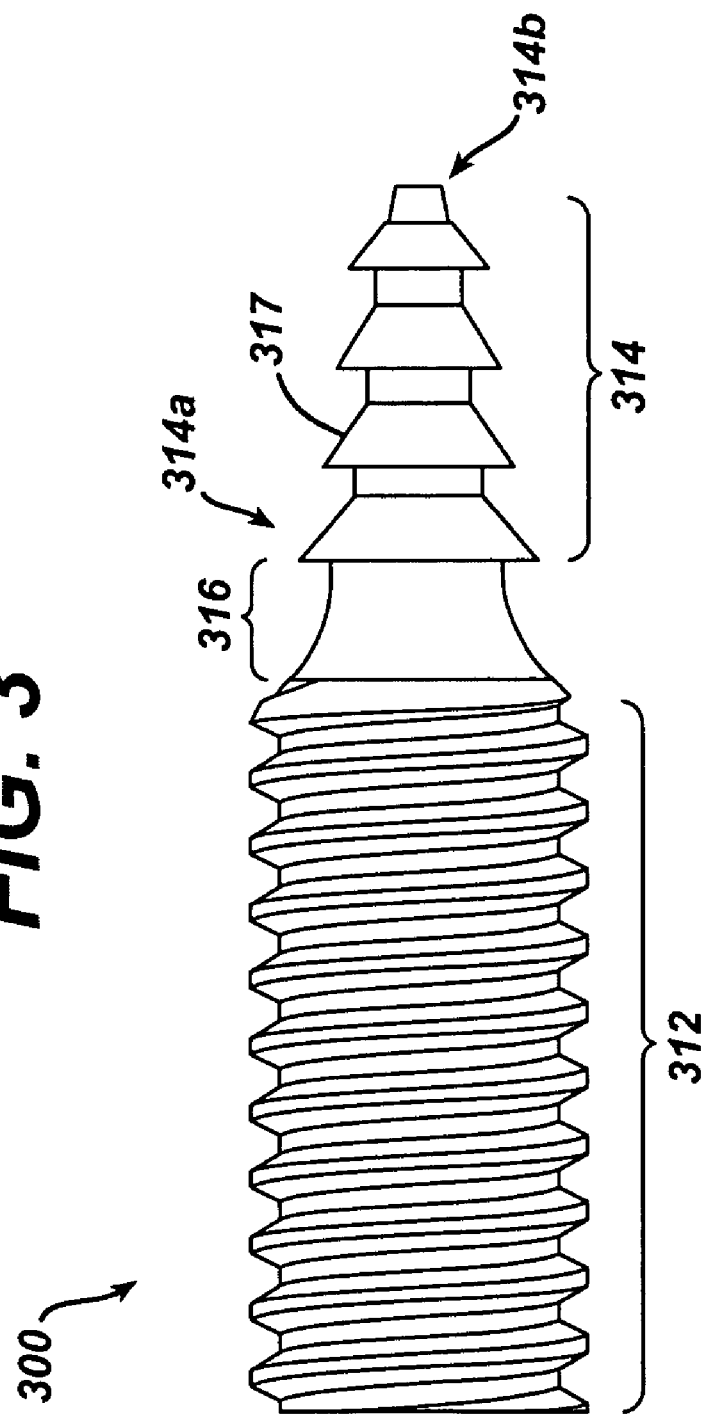
FIG. 3 is a perspective view of another embodiment of a bone screw having a distal portion with a stepped configuration.

FIG. 3 illustrates a bone screw 300 having a distal portion 314 with a diameter that decreases in a proximal-to-distal direction. The wedge-shaped distal portion 314 of the screw 300 can optionally include one or more surface features 317 formed thereon to engage the bone and to prevent back-out of the screw 300 once implanted. While the surface features can have virtually any configuration, FIG. 3 illustrates a wedge-shaped distal portion 314 having a stepped-configuration where it includes several annular ridges 317 formed thereon and adapted to engage bone. The annular ridges 317 preferably have a decreasing circumference from the distal end 314b to the proximal end 314a of the bone screw 300.

Figure 4:
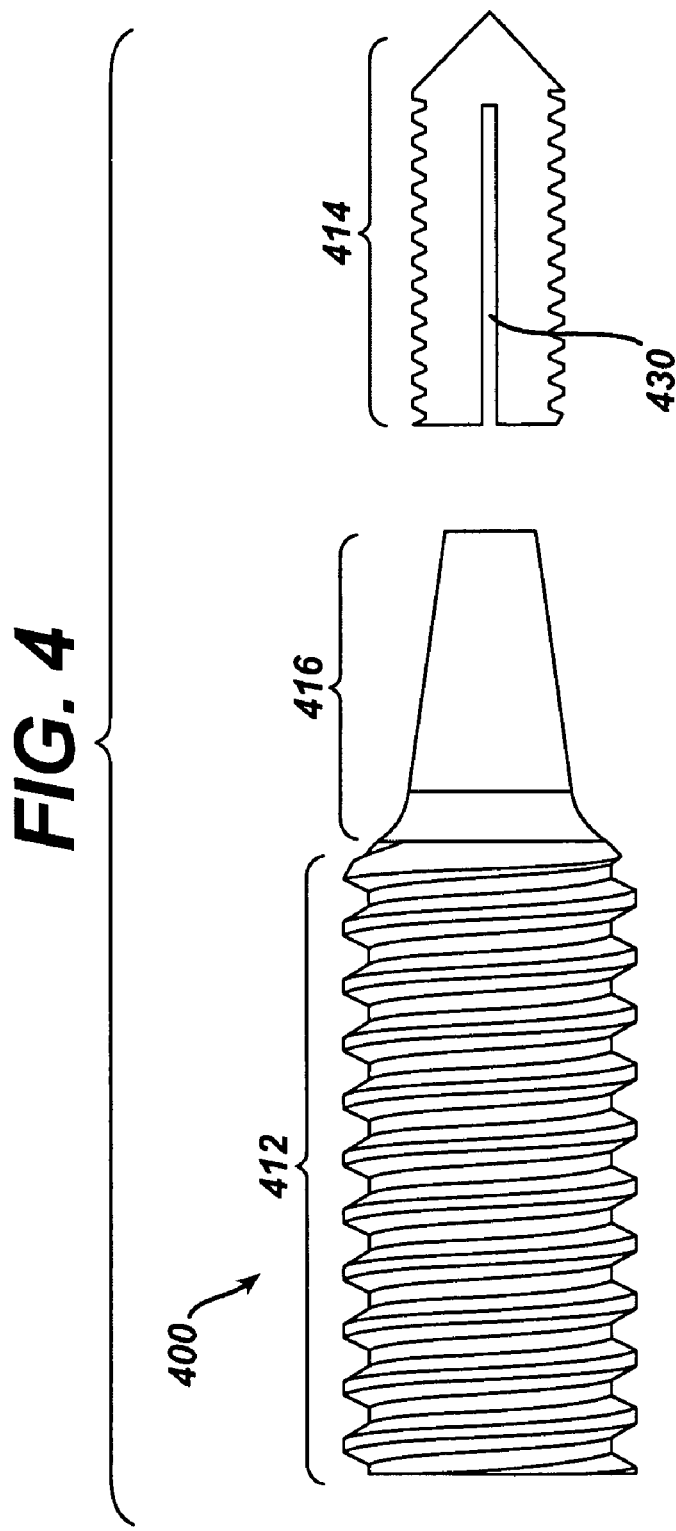
FIG. 4 is a perspective view of an expandable bone screw in accordance with another embodiment of the present invention.

Another bone screw 400 is shown in FIG. 4 having a distal portion 414 that is adapted to be expanded upon implantation. In particular, the bone screw 400 includes a proximal portion 412 having an extension member 416 extending distally therefrom, and a distal portion 414 that is adapted to receive the extension member 416. The extension member 416 of the proximal portion 412 can have virtually any shape, size, and configuration, but it should be adapted, upon insertion into the distal portion 414, to expand the distal portion 414. The distal portion 414 likewise can have virtually any shape, size, and configuration, but it should be adapted to expand upon receipt of the extension member 416 such that the distal portion 414 engages the bone tunnel. In an exemplary embodiment, the distal portion 414 includes at least one slot 430 extending along a portion thereof to allow the distal portion 414 to expand. In a further embodiment, the extension member 416 can be threaded (not shown) to mate with corresponding threads formed within the distal portion 414. While the distal portion 414 can be formed from a separate piece, the distal portion 414 can optionally be temporarily attached to the proximal portion 412 to facilitate implantation of the bone screw 300. A person skilled in the art will appreciate that the bone screw can have a variety of other configurations.

Figure 5:
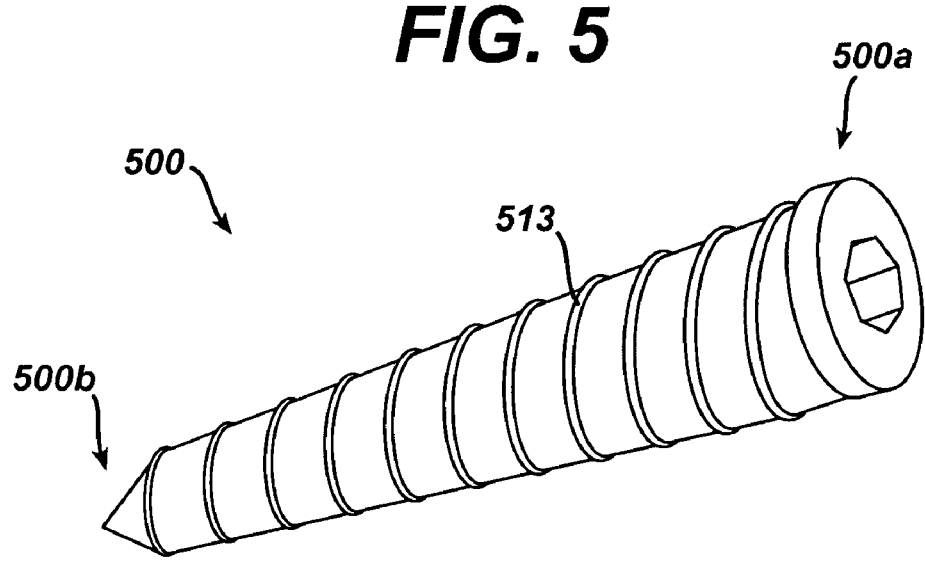
FIG. 5 is a perspective view of yet another embodiment of a bone screw in accordance with the present invention.

FIG. 5 illustrates yet another embodiment of a bone screw 500 having a single thread 513 formed thereon having a pitch that gradually decreases from the proximal end 500a to the distal end 500b of the screw 500. The actual shape and size of the screw shank can vary, but preferably both the major and minor diameters of the shank are tapered from a proximal end 500a to a distal end 500b. In use, the decreasing pitch of the thread 513 will produce the same effect as bone screw 10 described with respect to FIGS. 1A and 1B.

Figure 6A:
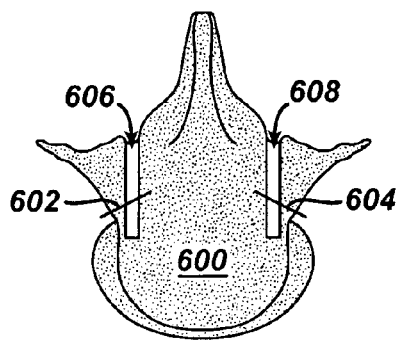
FIG. 6A illustrates a top view of a prepared vertebral body with dual diameter holes drilled in the pedicles for receiving a bone screw.

The bone screws of the present invention can be used in a variety of medical procedures to distract two segments of bone, but in an exemplary embodiment the bone screws are used to expand the spinal canal. FIGS. 6A-6D illustrate bone screw 10 in use. As shown in FIG. 6A, the pedicle of a vertebrae 600 is cut on both sides of the spinous process to form two gaps 602, 604. Two channels 606, 608 can also optionally be drilled in a posterior to anterior direction through the transverse process and into the pedicle for receiving a bone screw 10. Each channel 606, 608 preferably has a dual diameter for receiving the corresponding proximal and distal portions 12, 14 of the bone screw 10. More particularly, the posterior section of each channel 606, 608 preferably has a larger circumference than the anterior section of each channel 606, 608. Drill bits having different sizes can be used to achieve a dual diameter channel.

Figure 6B:
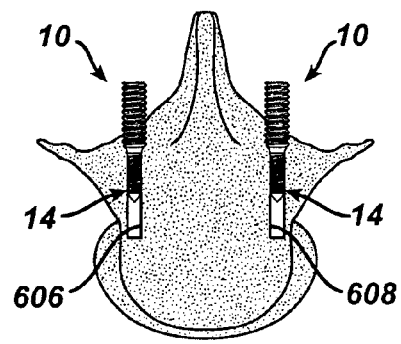
FIG. 6B illustrates the distal threads of two bone screws engaging the anterior portion of the vertebral body after the proximal threads have engaged the posterior portion.
Figure 6C:
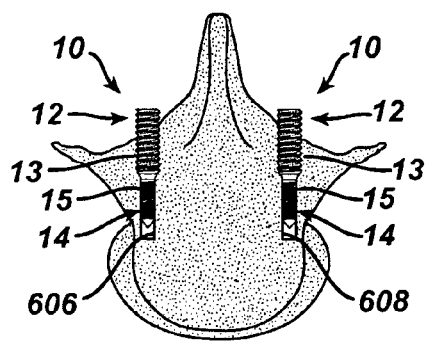
FIG. 6C illustrates the expansion of the spinal canal between the gaps in the pedicles as both threaded portions of the bone screws are engaged in bone.
Figure 6D:
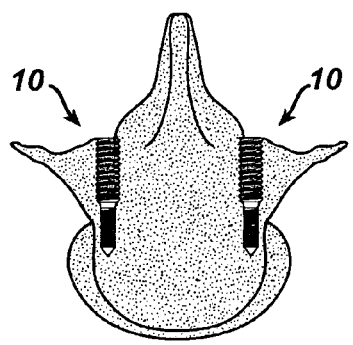
FIG. 6D shows the bone screws fully seated and the spinal canal in its expanded state.

As shown in FIG. 6B, a bone screw 10 is then inserted into each pre-drilled channel 606, 608 in the pedicle using a driver tool (not shown). As the screw 10 is threaded into the channel 606, 608, the distal portion 14 advances through the posterior portion of the pedicle without engaging the bone. The screw 10 is designed such that the distal portion 14 passes through the posterior portion of the channel 606, 608 and the proximal thread 13 engages the posterior portion of the channel 606, 608 first. When the distal thread 15 reaches the anterior portion of the channel 606, 608, the thread 15 begins to engage the anterior portion of the bone, as shown in FIG. 6C. Because the distal thread 15 has a smaller pitch $P_2$ than the pitch $P_1$ of the proximal thread 13, the distal portion 14 advances slower than the proximal portion 12 of the screw 10. This imparts a distracting force between the anterior and posterior portions of the vertebrae, thereby separating the anterior and posterior portions of the vertebrae as the screw 10 is driven into the vertebrae. As a result, the spinal canal is expanded as shown in FIG. 6D.

The bone screw 10 of the present invention can be formed from a variety of biologically compatible materials, or a combination of materials, including, for example, bioabsorbable and/or non-bioabsorbable materials. Suitable materials include, for example, osteoconductive material or cadaver bone, such as cortical bone. In an exemplary embodiment, the threads 13, 15 along the proximal and distal portions 12, 14 are formed from cancellous bone, but they could also be formed from cortical bone depending on the area of intended use. Other suitable materials include, for example, metals such as stainless steel, titanium, and carbon fiber reinforced polymers or polyethylethylketone.

In another embodiment, the bone screw 10, or a portion of the bone screw 10, can be coated with or formed from a bone-growth promoting material. Examples of such materials include hydroxyapatite, calcium phosphate, and other materials such as bioactive glasses, plasmas, ceramics, porous materials, and combinations thereof. The bone screw 10, or a portion of the bone screw 10, can also optionally or alternatively be injected with bone growth factors, such as stem cell concentrations and/or platelet rich substances.

A person skilled in the art will appreciate that while the implant illustrated herein is described for use with spinal surgery, the implant can be adapted for use with a variety of medical procedures. Accordingly, the invention is not to be limited by what has been particularly shown and described, except as indicated by the appended claims. All publications and references cited herein are expressly incorporated herein by reference in their entirety.

What is claimed is:

1. A bone screw comprising:
    a shank having
        a proximal portion having at least one thread formed thereon, the at least one thread having a first pitch in a proximal region of the proximal portion and a second pitch in a distal region of the proximal portion,
        a distal portion having at least one thread formed thereon, the at least one thread having a third pitch, and
        a thread-free region formed between the proximal and distal portions;
    wherein the second pitch is greater than or equal to the third pitch and is less than the first pitch.

2. The bone screw of claim 1, wherein the third pitch is less than the first pitch.

3. The bone screw of claim 1, wherein the at least one thread in the distal region of the proximal portion is shaped to inhibit back-out of the screw when the screw is implanted in bone.

4. The bone screw of claim 1, wherein the at least one thread on the proximal portion comprises a single thread extending between the proximal and distal regions of the proximal portion.

5. The bone screw of claim 1, wherein the at least one thread on the proximal portion comprises a first thread formed on the proximal region of the proximal portion and a second thread formed on the distal region of the proximal portion.

6. A method of expanding the spinal canal, comprising:
    providing a bone screw having a shank including proximal and distal portions that are configured to create a distraction force therebetween when inserted into two segments of bone;
    forming a hole in the pedicle of a vertebral body adjacent to the spinous process;
    cutting the pedicle across the hole and adjacent to the vertebral body to form two bone portions;
    advancing the bone screw into the hole, wherein the proximal and distal portions of the bone screw expand the distance between the two bone portions.

7. The method of claim 6, wherein at least one of the proximal and distal portions includes a thread formed thereon.

8. The method of claim 6, wherein the proximal and distal portions each include a thread formed thereon, and wherein the thread on the distal portion has a pitch that is less than a pitch of the thread on the proximal portion.

9. The method of claim 6, wherein the proximal portion includes a thread formed thereon that has a pitch that varies along a length of the proximal portion.

10. The method of claim 6, wherein at least a portion of the bone screw is coated with or formed from a bone growth-promoting material.

11. The method of claim 6, wherein the bone screw further includes a driver receiving element located on a proximal end of the proximal portion of the shank.

* * * * *